(12) United States Patent
Baumann et al.

(10) Patent No.: US 9,447,245 B2
(45) Date of Patent: Sep. 20, 2016

(54) CROSS-LINKING AND STABILIZATION OF ORGANIC METAL COMPLEXES IN NETWORKS

(75) Inventors: Thomas Baumann, Karlsruhe (DE); Tobias Grab, Karlsruhe (DE); Michael Bächle, Karlsruhe (DE); Daniel Volz, Karlsruhe (DE)

(73) Assignee: CYNORA GMBH, Bruchsal (DE)

(*) Notice: Subject to any disclaimer, the term of this patent is extended or adjusted under 35 U.S.C. 154(b) by 0 days.

(21) Appl. No.: 14/131,594

(22) PCT Filed: Jul. 9, 2012

(86) PCT No.: PCT/EP2012/063446
§ 371 (c)(1),
(2), (4) Date: Jan. 8, 2014

(87) PCT Pub. No.: WO2013/007709
PCT Pub. Date: Jan. 17, 2013

(65) Prior Publication Data
US 2014/0142258 A1 May 22, 2014

(30) Foreign Application Priority Data

Jul. 8, 2011 (EP) ..................................... 11173374
Jul. 22, 2011 (EP) ..................................... 11175122

(51) Int. Cl.
*C08G 79/14* (2006.01)
*C07F 1/08* (2006.01)
(Continued)

(52) U.S. Cl.
CPC ................. *C08G 79/14* (2013.01); *C07F 1/08* (2013.01); *C07F 9/587* (2013.01); *C08F 8/30* (2013.01);
(Continued)

(58) Field of Classification Search
CPC ...... H05B 33/14; H01L 51/009; C08G 79/14
USPC .......................................................... 525/539
See application file for complete search history.

(56) References Cited

U.S. PATENT DOCUMENTS 4,360,654 A * 11/1982 Hechtl .................. C07F 7/2252
528/18
4,647,680 A * 3/1987 Barfurth ................ C07F 7/006
427/126.1

(Continued)

FOREIGN PATENT DOCUMENTS

CN 201280034048.3 4/2015
DE 3337100 A1 5/1985
(Continued)

OTHER PUBLICATIONS

International Search Report and Written Opinion of International Searching Authority for PCT/EP2012/063446 dated Feb. 8, 2013.
(Continued)

*Primary Examiner* — Mike M Dollinger
(74) *Attorney, Agent, or Firm* — Ryan, Mason & Lewis, LLP

(57) ABSTRACT

The invention relates to the preparation of an organic transition metal complex cross-linked into a multi-dimensional network, comprising the performance of a first reaction, which comprises a first reactant in the form of an organic metal complex and a second reactant for the formation of a multi-dimensional network, where the organic metal complex is cross-linked to form the multi-dimensional-network during the reaction.

8 Claims, 5 Drawing Sheets

(51) Int. Cl.
*H01L 51/00* (2006.01)
*H05B 33/14* (2006.01)
*C08F 12/26* (2006.01)
*C08F 212/08* (2006.01)
*C08F 212/14* (2006.01)
*C08F 8/30* (2006.01)
*C08F 8/40* (2006.01)
*C08F 8/42* (2006.01)
*C09K 11/06* (2006.01)
*C07F 9/58* (2006.01)
*H01L 51/50* (2006.01)

(52) U.S. Cl.
CPC . *C08F 8/40* (2013.01); *C08F 8/42* (2013.01); *C08F 12/26* (2013.01); *C08F 212/08* (2013.01); *C08F 212/14* (2013.01); *C09K 11/06* (2013.01); *H01L 51/004* (2013.01); *H01L 51/009* (2013.01); *H01L 51/0091* (2013.01); *H05B 33/14* (2013.01); *C09K 2211/188* (2013.01); *H01L 51/0043* (2013.01); *H01L 51/5016* (2013.01); *Y02E 10/549* (2013.01)

(56) References Cited

U.S. PATENT DOCUMENTS

| | | | |
|---|---|---|---|
| 4,756,848 A | 7/1988 | Tieke et al. | |
| 5,395,887 A * | 3/1995 | Gondard | C08G 18/838 525/123 |
| 7,858,724 B2 * | 12/2010 | Kanitz | C07F 15/0033 528/394 |
| 2004/0247934 A1 | 12/2004 | Takeuchi et al. | |
| 2006/0269779 A1 | 11/2006 | Takahashi et al. | |
| 2009/0069548 A1 | 3/2009 | Poulter et al. | |
| 2011/0089411 A1 * | 4/2011 | Xia | H01L 51/002 257/40 |
| 2012/0267612 A1 * | 10/2012 | Xia | C08G 61/12 257/40 |

FOREIGN PATENT DOCUMENTS

| | | |
|---|---|---|
| DE | 69021559 T2 | 1/1996 |
| EP | 0050358 A2 | 4/1982 |
| EP | 0190998 A1 | 8/1986 |
| JP | S57112399 A | 7/1982 |
| JP | S61183295 A | 8/1986 |
| JP | H06502877 A | 3/1994 |
| JP | 2008537943 A | 10/2008 |
| JP | 2014506725 A | 3/2014 |
| WO | 2006107903 A2 | 10/2006 |
| WO | 2010082924 A1 | 7/2010 |
| WO | 2010149748 A1 | 12/2010 |
| WO | 2011067401 A1 | 6/2011 |
| WO | WO2012098263 A1 | 7/2012 |

OTHER PUBLICATIONS

B. Ma et al., "Multifunctional Crosslinkable Iridium Complexes as Hole Transporting/Electron Blocking and Emitting Materials for Solution-Processed Multilayer Organic Light-Emitting Diodes," Advanced Functional Materials, Apr. 2009, pp. 1024-1031, vol. 19, No. 7.

N. Holten-Andersen et al., "pH-Induced Metal-Ligand Cross-Links Inspired by Mussel Yield Self-Healing Polymer Networks with Near-Covalent Elastic Moduli," Proceedings of the National Academy of Sciences (PNAS), Feb. 2011, pp. 2651-2655, vol. 108, No. 7.

D. Volz et al., "New Coppertunities: Auto-Catalyzed Crosslinking and Modification of Copper-Emitters for OLEDs," 4th Internatinoal Conference and Exhibition for the Organic and Printed Electronics Industry (LOPE-C), Jun. 2012, pp. 1-2.

D. Volz et al., "Auto-Catalysed Crosslinking for Next-Generation OLED-Design," Journal of Materials Chemistry, Sep. 2012, pp. 20786-20790, vol. 22, No. 38.

Riedl/Janiak, "Anorganische Chemie," XP-002666355, 2007, p. 306.

* cited by examiner 25 26 distribution around the most frequent value in nm,
relative position of the graph at random

CROSS-LINKING AND STABILIZATION OF ORGANIC METAL COMPLEXES IN NETWORKS

FIELD OF INVENTION

The invention relates to organic transition metal complexes and their cross-linking into a multi-dimensional network. In particular, the invention relates to a method for the production of an organic transition metal complex, which is cross-linked in a multi-dimensional network by formation of covalent bonds.

BACKGROUND OF THE INVENTION

Due to their properties, phosphorescent transition metal complexes become more and more important as highly efficient emitters in optoelectronic components such as OLEDs. The spin-orbit coupling induced by the transition metal atom (heavy metal atom) results in an increased intersystem-crossing rate from the excited singlet state to the triplet state and thus in the use of the singlet excitons as well as the triplet excitons for emission and thereby allows a theoretical achievable internal quantum yield of 100%.

These phosphorescent dyes are usually introduced into appropriate energetically adjusted host materials. Polymeric structures are particularly suitable for this purpose due to the ease of processing by liquid processing from solution. Ideally, these should fulfill additional functions such as the spatial separation of the dye molecules to prevent undesirable concentration quenching processes and triplet-triplet-annihilation under emission reduction, increased charge carrier injection and transport and an increased recombination probability directly on the emitter molecules.

Thus, the combination of suitable polymeric host structures with appropriate statistically blended emitter compounds and additionally inserted charge transport molecules represents a method diversely used for the preparation of polymeric light emitting diodes (PLEDs). Even though the OLED components produced this way have mostly high efficiencies, these mixed systems can be subject to undesired phase separations, aggregations or crystallization processes, which have a negative effect on the capacity and the lifetime of the components. Therefore, the production of adapted (co)polymers, which fulfill different functions such as charge transport and emission while at the same time using the advantages of liquid processing, is of steadily increasing interest.

For the synthesis of phosphorescent polymers with directly attached transition metal complexes, two different routes are in principle available in the prior art: on the one hand, the attachment of the metal complexes to the polymers provided with functional groups, which were prepared before ("complexation at the polymer"), and on the other hand, the polymerization of corresponding monomers, which carry the metal complexes ("polymerization of complex monomers").

The first strategy allows a modular design with the basic attachment of a large amount of different metal complexes to the polymer and has as an advantage the extensive and more detailed analysis of the metal-free polymers synthesized before by common polymer analysis such as, for example, GPC and NMR. Additionally, the amount of metal complex in the final polymer can theoretically be varied by careful adjustment of the potential coordination sites. The use of functionalization methods orthogonal to the actual polymerization reactions, which also have to proceed in high yields, is necessary for the success of the modular post-polymerization method.

The advantage of the second route consists of the controlled structure and quantitative functionalization of the metal complexes by using common polymerization methods, which in part must be adjusted to the correspondent metal complex-functionalized monomers and whose accurate characterization by common analytical methods is not possible in most cases due to the attached metal complexes.

Both methods have in common that the efficient emitter complexes are attached to a polymeric host system and can thus can be applied to liquid processing; nevertheless, they are subject to the disadvantages of a possible multi-layer arrangement: The low-cost liquid-processing of polymers allows no simple sequential application of defined, thin layers. This is due to the general solubility of the polymeric materials. A relatively high amount of solvent is necessary for the desired material thickness and already dried layers are partly dissolved again during the application of subsequent layers, whereby the necessary layer arrangement is broken again.

Previous solutions to this problem are the development of cross-linkable materials with negative photoresist-like properties, which are cross-linked after deposition out of solution by exposure to light or thermal treatment, and thus form insoluble layers. Fréchet and co-workers reported, for example, on a number of cross-linkable heteroleptic Ir(III) complexes for the application in liquid-processable phosphorescent OLEDs, which carry two cross-linkable vinyl-benzyl ether units, which can be fully cross-linked by heating to 180° C. (*Multifunctional Crosslinkable Iridium Complexes as Hole Transporting/Electron Blocking and Emitting Materials for Solution-Processed Multilayer Organic Light-Emitting Diodes*, Biwu Ma, Bumjoon J. Kim, Daniel A. Poulsen, Stefan J. Pastine, Jean M. J. Fréchet, *Adv. Funct. Mater.* 2009, 19, 1024-1031). The cross-linked films show high solvents resistance and very good properties for the formation of films, making the principle preparation of multi-layer systems by sequential liquid processing of different layers possible. However, this approach represents no controlled build-up of well-defined metal complex-functionalized polymers since the polymerization proceeds only by thermal processes and completely uncontrolled. It is, for example, not possible to exactly adjust by controlled polymerization methods the molecular weight, the chain length, and the polydispersity of the polymer to operate reproducibly and to make adjustments according to the requirements of a standardized liquid-processing.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
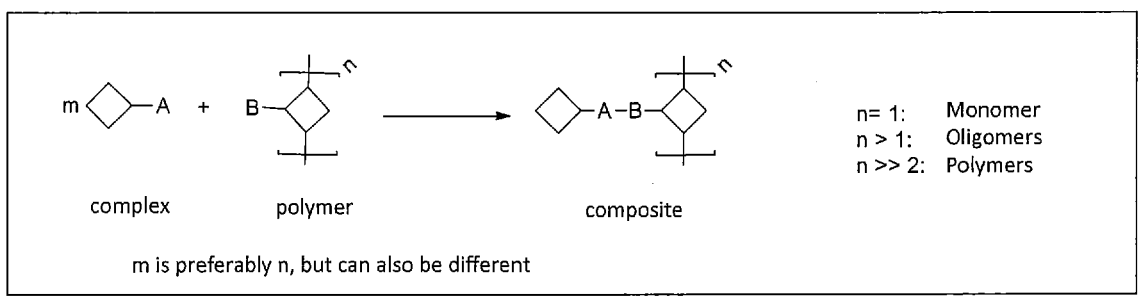
FIG. 1 shows the general scheme for the linkage of organic metal complexes (first reactant) with monomers, oligomers or polymers (second reactant), each carrying a corresponding anchor group which enables the cross-linking of the organic metal complex in accordance with an embodiment of the present invention.

Exemplary embodiments of the invention will now be discussed in further detail. This invention may, however, be embodied in many different forms and should not be construed as limited to the embodiments set forth herein.

In a first aspect, the invention relates to a method for the preparation of an organic transition metal complex cross-linked into a—preferably insoluble—multi-dimensional network. This method comprises the performance of a first reaction, which comprises the reaction of a first reactant in the form of an organic metal complex with a second reactant (different to the first reactant). The second reactant serves for the formation of a multi-dimensional network.

During this first reaction, the metal complex is being cross-linked into a multi-dimensional network by the formation of covalent bonds, i.e. at least two bonds of the ligand of the transition metal complex with the multi-dimensional network resulting from the second reactant are formed. This can be in its simplest shape a ladder-like (two-dimensional) structure, in which two network strings are linked by at least one transition metal complex, which forms via at least one ligand with one of the strings each at least one covalent bond. Covalent hereby means the bonding between nonmetal elements. Furthermore, as product of the first reaction, complicated three-dimensional networks are possible, which comprise metal complexes cross-linked with a variable number of network strings. The cross-linked metal complex is thus immobilized in the multi-dimensional network.

For the covalent linkage of the organic transition metal complex to the second reactant suitable for the formation of a multi-dimensional network, different strategies are available. Usually, pairs of corresponding chemical groups, which can form a covalent chemical bond with each other, are used. These chemical groups, which are also referred to herein as anchor groups, belong to a first anchor group species or to a second anchor group species, wherein the anchor groups of the first anchor group species can form a covalent bond with the anchor groups of the second anchor group species. However, anchor groups of a first anchor group species cannot form a covalent bond among themselves and anchor groups of a second anchor group species cannot form a covalent bond among themselves. The cross-linking is not a (co)polymerization in which several monomers are cross-linked with each other.

According to a first preferred strategy of the covalent linkage of the organic transition metal complex to the second reactant, the transition metal complex comprises at least two anchor groups of a first anchor group species, which serve for the covalent binding of together at least two ligands of the transition metal complex into the multi-dimensional network. The second reactant comprises at least one anchor group of a second anchor group species, which is suitable for the binding of the second reactant to the first anchor group of the transition metal complex. The cross-linking of the transition metal complex into the multi-dimensional network is carried out by a reaction of the at least two anchor groups of the transition metal complex with one second anchor group each of a second reactant.

According to a second strategy of the covalent linkage of the organic transition metal complex to the second reactant, a third reactant, which can also be named "spacer" molecule, takes part in the first reaction.

Accordingly, the transition metal complex comprises at least two anchor groups of a first anchor group species, which is suitable for the covalent integration together at least two ligands of the transition metal complex into the matrix by a second anchor group. The second reactant comprises an anchor group of a first anchor group species, which serves for the binding of the second reactant to a second anchor group, so that the transition metal complex cannot bind directly to the second reactant. For the formation of a covalent bond between at least one ligand of the metal complex and the second reactant, a third reactant is added, which comprises two anchor groups of a second anchor group species, wherein each of these anchor groups of the third reactant can form a covalent bond with one first anchor group each (namely of the transition metal complex and of the second reactant). Thus, the cross-linking of the transition metal complex into the multi-dimensional network takes place by the reaction of the anchor group of the transition metal complex and by the reaction of the anchor group of the second reactant with the same third reactant.

The third reactant ("spacer" molecule) can be, for example, an alkyl chain of a desired chain length that comprises at two molecule parts spaced apart from each other, e.g. at ends opposite to each other, one anchor group each, which mediates the binding to the transition metal complex or to the second reactant. Besides alkyl chains, aryl, heteroaryl, alkenyl, alkinyl, trialkylsilyl and triarylsilyl groups and substituted alkyl, aryl, heteroaryl and alkenyl groups, optionally with substituents such as halogens, lower alkyl groups and/or electron donating and withdrawing groups, as well as common charge transport units such as, for example, arylamines, carbazoles, benzimidazoles, oxadiazoles etc. are also possible. The substituents can also lead to annulated ring systems.

Preferably, the metal complex and the second reactant are soluble in a common organic solvent (in particular for the production of OLED components). Besides alcohols, common organic solvents include ethers, alkanes as well as halogenated aliphatic and aromatic hydrocarbons and alkylated aromatic hydrocarbons, especially toluene, chlorobenzene, dichlorobenzene, mesitylene, xylene and tetrahydrofuran. In a preferred embodiment of the invention, the formed multi-dimensional network with cross-linked organic metal complexes is insoluble, which particularly makes the formation of a structure of several overlapping layers of such a multi-dimensional network possible in a simple manner.

Figure 2:
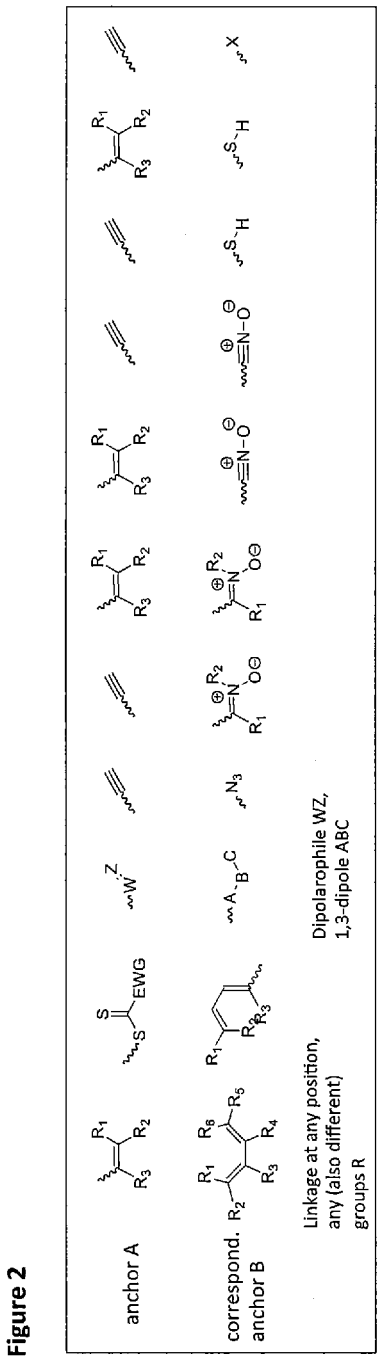
FIG. 2 shows selected examples of anchor groups of a first and a second anchor group species (each arranged in rows) in accordance with an embodiment of the present invention.

The first and the second anchor group may in particular be selected from the group of chemical groups shown in FIG. 2. If the metal complex is an emitter, the anchor group is preferably not conjugated to the emitter system in order not to affect the emission of the complex.

In principle, any organic transition metal complex which carries at least one of its ligands a first anchor group, but no main group metal or semi-metal, can be used in the method. In particular, besides the first anchor group, the metal complex comprises at least one metal center and at least one organic ligand. The metal complex can be mononuclear or polynuclear (di-, tri-, tetranuclear, etc.) and can carry one or several ligands. The ligands can be mono- or polydentate. If a mononuclear complex carries only one ligand, this ligand is polydentate. If the complex is not neutral, a corresponding counter ion has to be provided, which preferably does not take part in the first reaction as described herein.

During the occurring reaction, the ligands at the metal center are not exchanged or replaced by other ligands. The occurring reaction takes place exclusively directly at the ligand or in the ligand sphere, the basic structure of the metal complex remains unchanged.

The occurring reaction involves a covalent cross-linking, wherein the resulting new covalent bonds are preferably formed between non-metal elements.

Preferred organic metal complexes are, for example, light emitters, which can be applied in optoelectronic components, such as OLEDs. Another group of preferred metal complexes are semiconductors. Such emitting and semiconducting metal complexes are known in the art.

At least one ligand of the metal complex comprises a first anchor group. Taken together, a metal complex comprises two anchor groups, preferably of one anchor group species, which can be arranged at one ligand or are preferably distributed to two ligands of the metal complex. Thus, it is also possible that several ligands of a metal complex comprise one or several anchor groups, wherein the number of anchor groups at the metal complex and at the second ligand determines the degree of cross-linking.

The multi-dimensional network is a two-dimensional or three-dimensional network. A three-dimensional network is preferred.

The second reactant used in the method can be selected from a group consisting of a monomer, a oligomer and a polymer. Low-molecular, reactive molecules are here referred to as monomers, which can react to molecular chains or networks, to unbranched or branched polymers. Examples are common monomers such as styrene, ethylene, propylene, vinylchloride, tetrafluoro ethylene, acrylic acid methylester, methacrylic acid methylester, bisphenol A/phosgene, ethylene glycols, terephthalic acids and organochloro silanes. A molecule which is composed of 2 to 30 structurally identical or similar units is referred to as oligomer herein. Examples of oligomers are oligoethylene, oligopropylene, oligovinylchloride, oligotetrafluoro ethylene, oligoacrylic acid methylester, oligomethacrylic acid methylester, oligocarbonates, oligoethylene glycol, oligoethylene terephthalate, oligo(organo)siloxanes. Polymers are molecules that are composed of more than 30 structural identical or similar units. Examples of polymers are polystyrene, polyethylene, polypropylene, polyvinylchloride, polytetrafluoro ethylene, polyacrylic acid methylester, polymethacrylic acid methylester, polycarbonates, polyethylene glycol, polyethylene terephthalate, and poly(organo)siloxanes.

Thus, not only polymers but also lower molecular oligomers with two or more anchor groups of monomers can be linked, by means of which further functionalities can be brought into the periphery of the complexes, which opens new possibilities with regard to the charge transport and the charge carrier recombination in organic semiconductors. The term monomer includes in one embodiment lower molecular compounds, such as for example phosphoalkanes, phosphazenes, ferrocenylsilanes, and ferrocenylphosphines.

The cross-linking of a metal complex described herein has to be distinguished from the insertion of a complex into a polymer, wherein the complex is bound to one polymer string each and thus only the solubility characteristics of the attached complex change. Furthermore, to date, cross-linking is only known between polymers, which are not bound to metal complexes, wherein the polymers always react in a cross-linking reaction with themselves, thus are only homo-cross-linked. In contrast, according to the invention, cross-linking is only initiated by the formation of a bond to the metal complex, whereby the corresponding polymers are hetero-cross-linked to the metal complex.

In other words, the invention relates in one embodiment to materials, in particular to liquid-processable optoelectronic materials, which ensure due to their special structure both the covalent binding of a metal complex, for example a highly efficient emitter metal complex, to a functionalized second reactant such as to a monomer, oligomer or polymer, and its cross-linking and thus leading to its insolubility.

In a preferred embodiment of the invention, a fourth reactant is used in the first reaction of the method besides the metal complex, the second reactant and optionally the third reactant, wherein the fourth reactant is a hole or electron conducting chemical group and/or a charge blocking chemical group, which can also be cross-linked as a charge transport unit or a charge blocking unit. Examples for hole or electron conducting chemical groups are arylamines such as N,N'-bis(naphthalene-1-yl)-N,N'-bis(phenyl)-benzidine, N,N'-bis(naphthalene-1-yl)-N,N'-bis(phenyl)-2,2'-dimethylbenzidine, carbazoles such as 4,4-bis(carbazole-9-yl)biphenyl, 1,3-bis(carbazole-9-yl)benzene, benzimidazoles such as 1,3,5-tris(1-phenyl-1H-benzo[d]imidazole-2-yl)benzene, oxadiazoles such as 2-(4-biphenyl)-5-(4-tert-butylphenyl)-1,3,4-oxadiazole, triazoles such as 3-(4-biphenyl)-4-phenyl-5-tert-butylphenyl-1,2,4-triazole, 4-(naphthalene-1-yl)-3,5-diphenyl-4H-1,2,4-triazole.

The fourth reactant also comprises at least one anchor group of the first and/or the second anchor group species for the binding into the multi-dimensional network, depending whether the fourth reactant shall be bound to the metal complex or to the second reactant.

The invention consists in a stabilization and cross-linking method of metal complexes by monomers, oligomers and polymers, which consist of one or several metals and one at least bidentate or several mono- or polydentate ligands. According to the invention, the organic metal complex and the second reactant carry complementary chemical anchors of a (first or second) anchor group species, which are covalently bound to each other in a reaction proceeding as fast and completely as possible. Thereby, for example, luminescent or semiconducting metal complexes can be immobilized, e.g for applications in organic electronics, in order to increase the lifetime and long-term stability of the correspondent components.

Preferred are energetically favored reactions, referred to in the art as "click chemistry", which proceed specifically and result in a single product (H. C. Kolb, M. G. Finn, K. B. Sharpless, *Angew. Chem. Int. Ed.* 2001, 40, 2004-2021). Thus, the "click chemistry" comprises reactions, which are performable with high yields, are applicable in a broad range of applications, proceed (stereo)specifically, comprise simple reactions conditions (preferably insensitive to water and oxygen), comprise easily removable, as nonhazardous as possible side products and reagents (if at all), proceed in environmentally friendly and/or easily removable solvents such as water or without solvents and/or need a simple purification (extraction, phase separation, distillation or crystallization—preferably no chromatography) or no purification at all.

"Click" reactions are in most cases highly thermodynamically favored with often more than 20 kcal mol$^{-1}$, leading to a single product with fast conversions and high selectivity. In most cases, carbon heteroatom bonds are formed with click reactions.

According to the invention, in particular nucleophilic substitutions, especially ring opening of tense electrophilic heterocycles such as epoxides and aziridines, carbonyl chemistry of the "non-aldol" type such as the formation of aromatic heterocycles or hydrazones, additions to carbon-carbon double bonds such as the oxidative formation of epoxides and aziridines, dihydroxylation and Michael additions as well as cycloadditions to unsaturated C—C bonds, in particular 1,3-dipolar cycloadditions and Diels-Alder reactions can be applied. Further examples for such reactions are cross-coupling reactions for the formation of C—C bonds such as the Ullmann reaction, the Sonogashira reaction and the Glaser coupling. All of these reactions are known to a person of skill in the art.

In the context of the invention, particularly such reactions are relevant which do not need the addition of another reactant (i.e. a reactant other than the first, second and, if applicable, the third and, if applicable, the fourth reactant). Examples for such reactions are, besides the 1,3-bipolar cycloadditions and Diels-Alder reactions mentioned above, nitrone-alkyne reactions, nitril oxide-alkyne reactions, thiol-ene reactions, thiol-yne reactions, thiol-isocyanite reactions, tetrazole-alkene reactions and other methods known as click reactions in the chemical literature.

Figure 3:
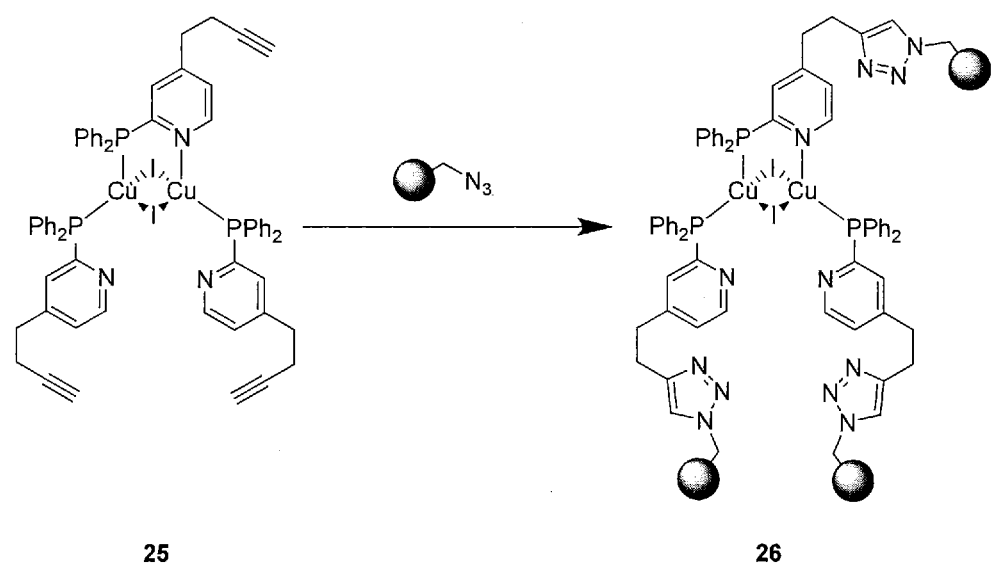
FIG. 3 shows an example reaction for the linking of an alkene substituted copper complex with a polymeric azide as second reactant in accordance with an embodiment of the present invention.

In a preferred embodiment of the method, the reaction takes place in the presence of a catalyst for the catalysis of the reaction. The catalyst is educt/reactant and at the same time catalyst. Preferably, the metal complex comprises the catalyst, i.e. the transition metal center contained in the organic metal complex serves also as a catalyst, so that a self-catalyzed cross-linking takes place. As an example, the copper-catalyzed click reaction between a terminal or activated alkyne as first anchor group of a first anchor group species and an azide as anchor group of a second anchor group species is shown in FIG. 3.

For example, the classic 1,3-dipolar cycloaddition (Huisgen cyclization), which otherwise needs rather high temperatures, proceeds non-regiospecifically and thus is generally not suited as "click" reaction (V. V. Rostovtsev, et al., *Angew. Chem. Int. Ed.* 2002, 41, 2596-2599; C. W. Tornøbe, et al., *J. Org. Chem.* 2002, 67, 3057), proceeds using a Cu(I) catalyst compared to the classic cyclisation up to $10^7$ times faster, regioselective (only the 1,4-regioisomer is formed), also in water, at room temperature and is thereby insensitive to most other functional groups such as, for example, alcohols, acids and acid derivatives, carbonyl compounds, halogens, etc.

The catalyst can, for example, be produced in situ from a Cu(II) species. CuSO$_4$ with sodium ascorbate or Cu(0) as reduction agent can be used, but other stabilized Cu(I) salts and complexes are also possible. In a preferred embodiment, the metal complex is a Cu(I) or a Cu(II) complex, so that the reaction takes place self-catalytically. Other possible catalysts are Pt, Pd, Ru, Au and Ag.

The reaction between metal complex and second reactant proceeds preferably at a temperature which is higher than room temperature. At least 50° C. are preferred, particularly preferred are temperatures from 80° C. to 120° C. The reaction time needed at the particular reaction temperature can be easily determined by a person skilled in the art. Usually, a reaction time of 1 minute to 60 minutes, preferably of 10 minutes to 30 minutes is to be anticipated, so that the metal complex is immobilized and thus stabilized and insoluble. The thermal activation can also be carried out by exposure to microwaves, whereby the reaction times can be shortened considerably to less than 1 minute.

Besides a thermal activation of the reaction of the method, in one embodiment of the invention, a photochemical activation takes place. This leads in comparison to the thermal activation mostly to shortened reaction periods, which can be less than 1 minute. Therefore, a photochemical activated reaction can also be performed without catalyst. A reaction in the presence of a catalyst is also possible.

If an anchor group, for example an alkyne linker, is present in conjugation to an organic ligand of the metal complex and an aromatic azide is used as complementary anchor group, the emission colors of such emitting complexes, which are based on charge transfer transitions between the metal ions and the ligands, can be influenced. In this context, metal complexes with three or more ligands (e.g. four, five or six ligands) are preferred, since thereby three or more linking positions (e.g. four, five or six linking positions) are present. Thus, the complexes can thereby be linked to the polymers as well as bound to hole or electron conductors (fourth reactants). The optical, mechanical and electrical properties of the obtained substances can thus be influenced by the particular composition of the azide mixture.

By means of the method described herein, it is possibly to easily arrange several stacked layers of immobilized metal complexes, without the need for using, for example, orthogonal solvents.

For the production of a multi-layer arrangement, a second reaction is performed after the first reaction described above. This second reaction comprises a fifth reactant in the form of an organic metal complex and a sixth, preferably soluble reactant for the formation of a preferably insoluble multi-dimensional network, wherein the metal complex is cross-linked during the second reaction in the forming multi-dimensional network by formation of covalent bonds. With regard to special embodiments of the second reaction, aspects described for the first reaction apply here analogously.

Thereby, the fifth reactant of the second reaction can be identical to or different from the first reactant of the first reaction. Likewise, the sixth reactant of the second reaction can be identical to or different from to the second reactant of the first reaction.

The cross-linking that occurs according to the invention allows for a fast and simple alignment of any number of photoactive layers, whose solubility does not have to be adjusted exactly to each other as in previous systems. This results in a considerable simplification of the processing, since the selection of the individual active layers does no longer have to be orthogonal to each other with regard to solubility, but can be combined almost independently from each other. This allows for the sequential application of any number of different layers and thereby leads to a significant increase of efficiency and durability.

In a preferred embodiment of the method, the anchor groups of the first and the second anchor group species are present in equimolar amounts, so that all anchor groups can form covalent bonds with complementary anchor groups.

According to a second aspect, the invention relates to an organic metal complex cross-linked into a multi-dimensional network, which is producible by a method described herein.

In particular in cases in which the metal complex is an emitter metal complex, which can and shall be applied in optoelectronic components, an advantage of the invention is the stabilization of the geometry of the emitter metal complex by the immobilization through cross-linking.

It is known that a change of geometry of an emitter complex by excitation from the ground state to the first excited state leads to greater shifts of the energy potentials and to higher possibilities for non-radiative relaxation processes. Therefore, the geometry of the excited state should not differ from that of the ground state. Thus, the spatial/sterical stabilization of emitters achieved by use of the invention leads to an increase in efficiency of emitters as metal complexes.

Due to the anchor groups for the linking click-reactions that are attached in the periphery of the ligands of the metal complexes, e.g. as emitter complexes, the possible movement of the ligands of the metal complexes to each other is highly limited. Thus, the complexes are fixed and stabilized. The transition probabilities for non-radiative processes are reduced by rotation and twisting in contrast to "free" complexes: The emission quantum yields of the emitters are increased. Simultaneously, the fixation leads to maximal utilization of the energetic gap between the ground state and the first excited state. Hereby, in comparison to the "free", i.e. not cross-linked complex, a blue shift of the emission spectrum can take place, because the population of rotational and vibrational states is less probable and the energy difference between the ground state and the first excited state (direct vertical alignment of the potential curves, cf. Franck-Condon-principle) is maximized.

In addition to the layer stabilization and the possible integration of defined hole and electron conductors, the invention also improves the efficiency of optoelectronic components: Due to the sterical hindrance of the metal complexes, the overlapping integrals between states not used for emission decrease, the population of rotational and vibrational states become less likely. The stability of the complexes increases due to the prevention of bond breaking and non-radiative relaxations through free mobility of the ligands of a metal emitter system. By means of the immobilization, it is possible to shift the emission of a given free, i.e. not cross-linked, emitting metal complex in the direction to or into the blue spectral range.

According to a third aspect, the invention relates to the use of an organic metal complex cross-linked in a multi-dimensional network as an emitter or an absorber in an optoelectronic component, provided that the metal complex is a light emitter or a light absorber.

Accordingly, in a fourth aspect the invention relates to an optoelectronic component comprising a cross-linked organic metal complex, as described herein.

The optoelectronic component can be an organic light-emitting diode (OLEDs), a light-emitting electrochemical cell (LEECs or LECs), OLED sensors, optical temperature sensors, organic solar cells (OSCs), organic field effect transistors, organic diodes, organic photodiodes and "down conversion" systems. Such components are known to a person of skill in the art.

According to a fifth aspect, the invention relates to a method for the production of an organic metal complex cross-linked in a multi-dimensional network, in particular to a thin layer with a thickness of 75 nm to 300 nm, in particular 100 nm to 250 nm, particularly for the production of an optoelectronic component.

The method comprises at least the following steps: First, a mixture of a first reactant in the form of an organic metal complex and a second reactant, thus a means for the immobilization of the metal complex, is applied to a solid support. The metal complex is cross-linked in the forming multi-dimensional network by formation of covalent bonds during the performed first reaction of the first reactant with the second reactant.

As already described, the formation of the cross-linking is preferably carried out at higher temperatures, preferably between 80° C. to 120° C.

The application of the mixture of both reactants on a solid support can be carried out by means of all methods known in the state of the art, in particular by means of inkjet printing, dipping, spincoating, slot-die coating or knife coating.

According to a sixth aspect, the invention relates to the use of a cross-linked metal complex as an emitter material for an optoelectronic component, in particular as optoelectronic ink.

In a seventh aspect, the invention relates to an organic transition metal complex with at least one transition metal center and at least one ligand. According to the invention, the metal complex comprises two anchor groups of a first anchor group species for the reaction with an anchor group of a second anchor group species for cross-linking, wherein the anchor group of the metal complex can form a covalent bond with the anchor group of a second reactant, which serves for the formation of a multi-dimensional network, during the cross-linking reaction.

According to an eighth aspect, the invention relates to the use of such a metal complex for the cross-linking and immobilization of the metal complex to a second reactant, which comprises an anchor group of a second anchor group species.

In a ninth aspect, the invention relates to a method for the functionalization of an organic metal complex with two anchor groups through which the metal complex is bound to a second reactant carrying a second anchor group and can be immobilized, since the anchor groups of a first anchor group species of the metal complex react with the anchor group of a second anchor group species of the second reactant and can form a covalent bond.

In FIG. 1, the reaction product is referred to as composite herein.

In FIG. 2, the anchor groups shown opposite to each other can, bound on the one hand to the metal complex and on the other hand to the second reactant, form a covalent bond between the reactants and thus cross-link and immobilize the metal complex. First and second anchor group species are addressed here as anchor A and anchor B. Depending on the use, the anchor A shown here can represent the first or the second anchor group species and the anchor B can represent the second or the first anchor group species, respectively.

Meaning of the groups shown:

R1-R6 can each independently be hydrogen, halogen or substituents, which are bound via oxygen (—OR*), nitrogen (—NR*$_2$) or silicon atoms (—SiR*$_3$) as well as alkyl (also branched or cyclic), aryl, heteroaryl, alkenyl, akinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carbonyls, carboxylates and their esters, and $CF_3$ groups. R1-R6 can optionally also lead to annulated ring systems;

R*=organic group, selected from the group consisting of: hydrogen, halogen or deuterium, as well as alkyl (also branched or cyclic), aryl, heteroaryl, alkenyl, akinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and $CF_3$ groups;

X=halogen, $OSO_2Me$, $OSO_2Tolyl$, $OSO_2CF_3$.

In FIG. 3, the ball shown stands for polystyrene but can also represent any other polymer, oligomer or monomer as a second reactant.

Figure 4:
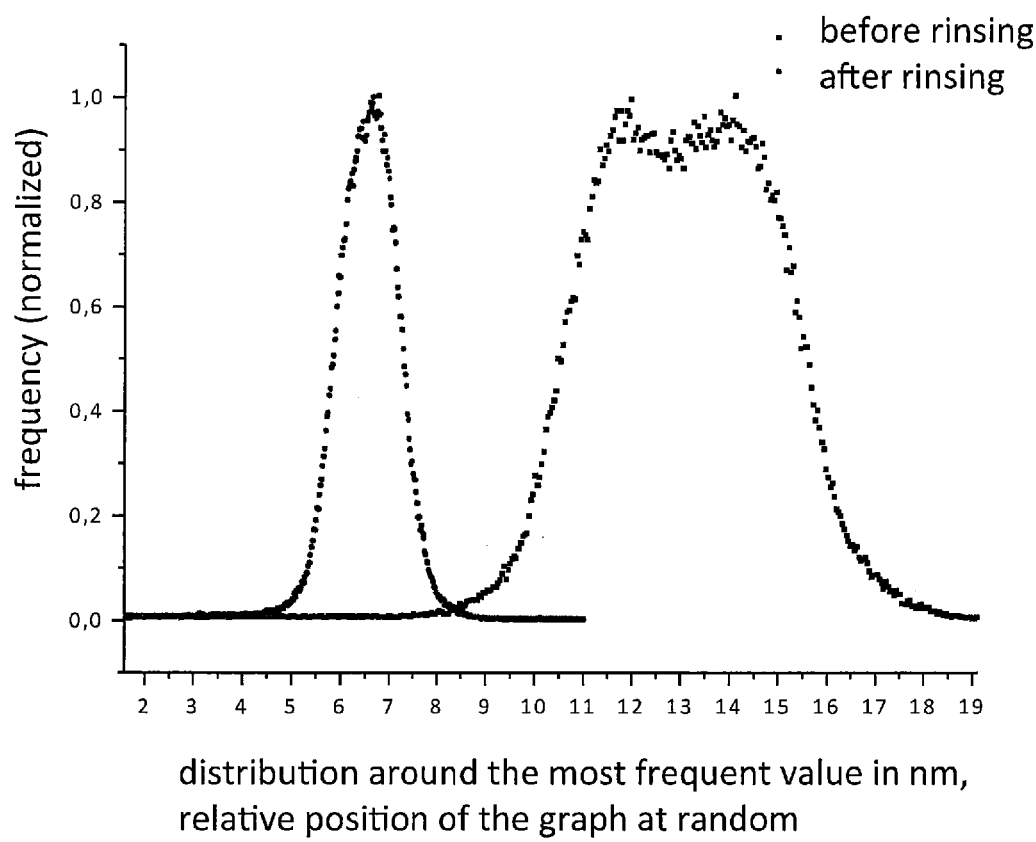
FIG. 4 shows a histogram of the AFM-picture before and after rinsing with xylene (see example 3) in accordance with an embodiment of the present invention.

In FIG. 4, the heights are normalized to 1, the position of the histograms on the X-axis is arbitrary, but true to scale. For a better overview, the histograms were not arranged on top of each other, but side by side. The processing was carried out at 40° C., the scan-size of the underlying images is 1 μm².

EXAMPLES

Example 1

In the described invention such reactions are preferred which do not need the addition of another reactant besides the metal complex and the second reactant, i.e. reactions that need at the most a catalyst that does not interfere with the further use. Examples for such reactions are 1,3-bipolar cycloadditions, Diels-Alder reactions, nitrone-alkyne reactions, nitril oxide-alkyne reactions, thiol-ene reactions, thiol-yne reactions, thiol-isocyanate reactions, tetrazole-alkene reactions and other methods known as click reactions in chemical literature.

Preferred are reactions which are catalyzed by the metal itself contained in the metal complex, which corresponds to a self-catalyzed cross-linking. One example is the copper-catalyzed click reaction between a terminal or activated alkyne and an azide. This reaction provides regioselectively and in high yields and conversions 1,4-triazoles (see FIG. 2).

Example 1.1

Cu Complex Catalyzed Click Reaction Between Terminal Alkynes and Azides

Phenylacetylene (103 mg, 1.0 mmol, 1.0 eq.) and benzyl azide (133 mg, 1.0 mmol, 1.0 eq.) were dissolved in an air-tight lockable vial with a septum in 10 mL dry dichloromethane. The Cu complex (catalytic or stoichiometric amounts) shown below was added, the vial sealed and the reaction stirred at room temperature for 2 days. For the removal of the catalyst complex the reaction mixture was put in 50 mL methanol and stirred for 20 min. The complex was removed by filtering and the filtrate was concentrated. Removal of the solvent and drying of the product in high vacuum resulted in the compound 1-benzyl-4-phenyl-1H-1,2,3-triazole as light yellow solid with 95% yield (245 mg, 0.95 mmol). The identity of the product was proven by NMR-spectroscopy, infrared spectroscopy and high-resolution mass spectroscopy.

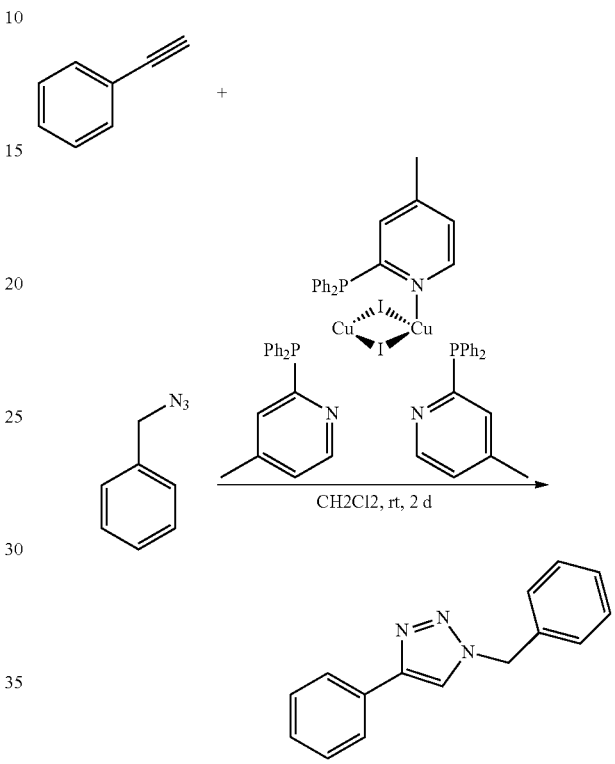

Example 1.2

Cu Complex Catalyzed Click Reaction Between Cu Alkyne Complex and Azides

The Cu complex (1.341 g, 1.0 mmol, 1.0 eq.) as first reactant was dissolved in an air-tight lockable vial with a septum in 10 mL dry dichloromethane and benzyl azide (466 mg, 3.5 mmol, 3.5 eq.) as second reactant was added. The reaction was stirred at room temperature for 12 hours, filtered over a syringe filter and precipitated by adding dropwise into diethyl ether. Rinsing of the precipitated solid with diethyl ether and drying of the product in high vacuum resulted in the compound tris-(4-(2-(1-benzyl-1H-1,2,3-triazol-4-yl)ethyl)-2-(diphenylphosphino)pyridin)-di-copper-diiodide as light green solid in 61% yield (1.052 g, 0.61 mmol). The identity of the product was proven by NMR-spectroscopy, infrared spectroscopy mass spectroscopy and elemental analysis.

Analogously the reaction was also conducted with further azides shown in table 1 as second reactant according to the same procedure.

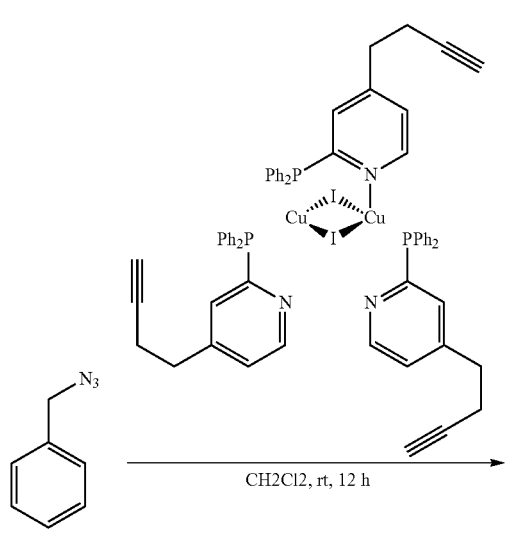
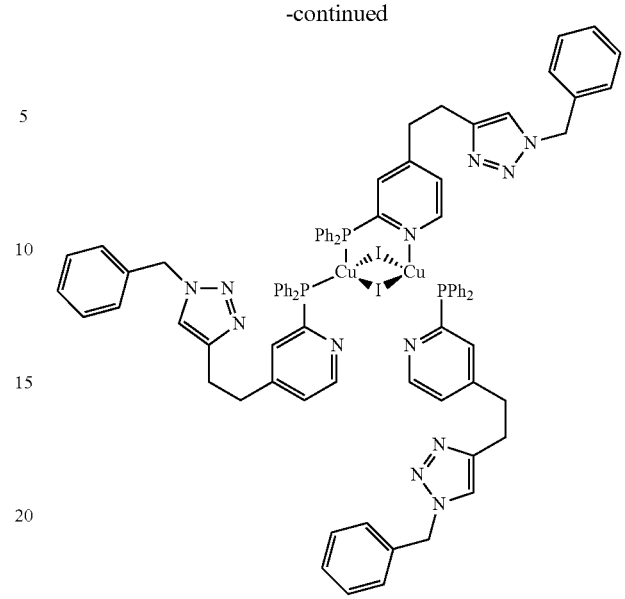

TABLE 1

Azides covalently bound to the Cu complex by click reaction and solubility of the products.

| Structure | Name | Preferred solubility of the product |
|---|---|---|
| (adamantyl-N₃) | Adamantyl azide | Ethyl acetate |
| N₃-CH₂CH₂-O-CH₂CH₂-O-CH₂CH₂-OH | 2-(2-(2-azidoethoxy)ethoxy)ethanol | DCM:EtOH = 1:1 |
| (4-vinylbenzyl azide) | 4-Vinylbenzyl azide | Toluene |
| (N-(4-azido-phenyl)-carbazole) | N-(4-Azido-phenyl)-carbazole | Toluene |
| (2-azido-glucose) | 2-Azido-glucose | MEOH:DCM = 1:1 |
| (phenyl azide) | Phenyl azide | Toluene |

TABLE 1-continued

Azides covalently bound to the Cu complex by click reaction and solubility of the products.

| Structure | Name | Preferred solubility of the product |
|---|---|---|
| (structure shown) | 6-(2-azido-acetamido)-O-peracetyl-galactose | |

Example 1.3

Cu Complex Catalyzed Click Reaction Between Cu Alkyne Complex and Polyazides for Cross-Linking The Cu complex (440 mg, 0.33 mmol, 1.0 eq.) was dissolved as first reactant in an air-tight lockable vial with a septum in 10 mL dry dichloromethane and converted with poly-(vinylbenzylazide-α/t-styrene) (370 mg, 1.0 mmol, 3.0 eq.) as second reactant. The reaction was stirred at room temperature for 12 hours, and the product precipitated as insoluble greenish solid from the reaction solution. The precipitate was withdrawn by suction, washed with 20 mL dichloromethane, 20 mL diethyl ether and 20 mL methanol and dried in high vacuum. The product poly-(4-(2-(1-(4-vinylbenzyl-1H-1,2,3-triazole-4-yl)ethyl)-2-(diphenylphosphino)pyridine)-alt-styrol @ CuI was a light green solid in 66% yield (540 mg, 0.21 mmol) and represents a cross-linked metal complex. The identity of the product was clearly proven by infrared spectroscopy, photoluminescence spectroscopy and elemental analysis.

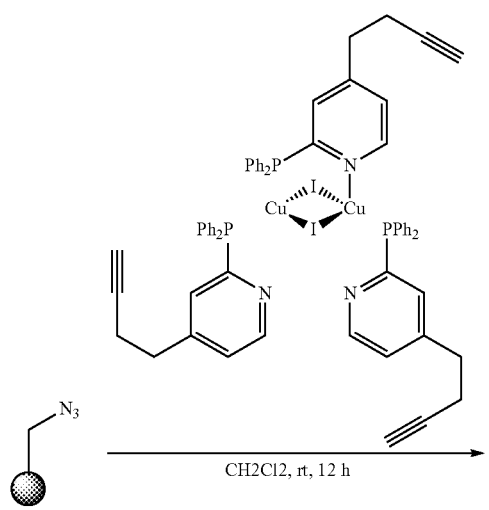

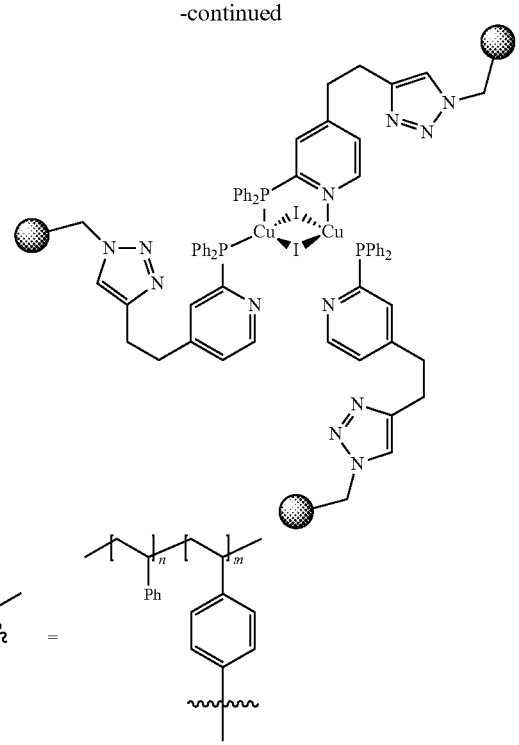

It was shown that such a reaction provides insoluble, cross-linked metal complexes (composite materials). Starting complex 25 as well as product 26 (see FIG. 2) show a yellow luminescence, whose spectrum is not further influenced or disturbed by the reaction since the anchor groups are not in conjugation to the emitter system.

After application onto a glass slide using a knife-coating apparatus (all other known printing or coating methods such as, for example, spin-coating, slot-die or ink-jet are also possible) in a thin layer and curing by heating to 100° C. for 30 minutes, this layer became stabilized and insoluble. Using this method, multilayer arrangements, which otherwise need orthogonal solvents or photochemical curing steps for implementation, can be easily realized. In addition, this cross-linking provides for a stabilization and fixation of the geometric structure of the metal complexes, preventing a movement of the ligands and thus a change in structure of the excited molecules and effectively inhibiting a reduction in efficiency due to non-radiative relaxation pathways.

Example 1.4

Cu Complex Catalyzed Click Reaction Between Cu Alkyne Complex and Polyazides with Polyethylene Glycol Scaffold for Cross-Linking The Cu complex (10 mg, 8.13 μM, 1.0 eq.) shown below was treated with a standard solution of polyglycidyl azide "GAP" in dry dichloromethane (1 mL of a 2440 mg/L solution, 3 eq. azide per eq. complex) and immediately afterwards a thin film produced by spin-coating. The film was stable against rinsing or immersion in toluene.

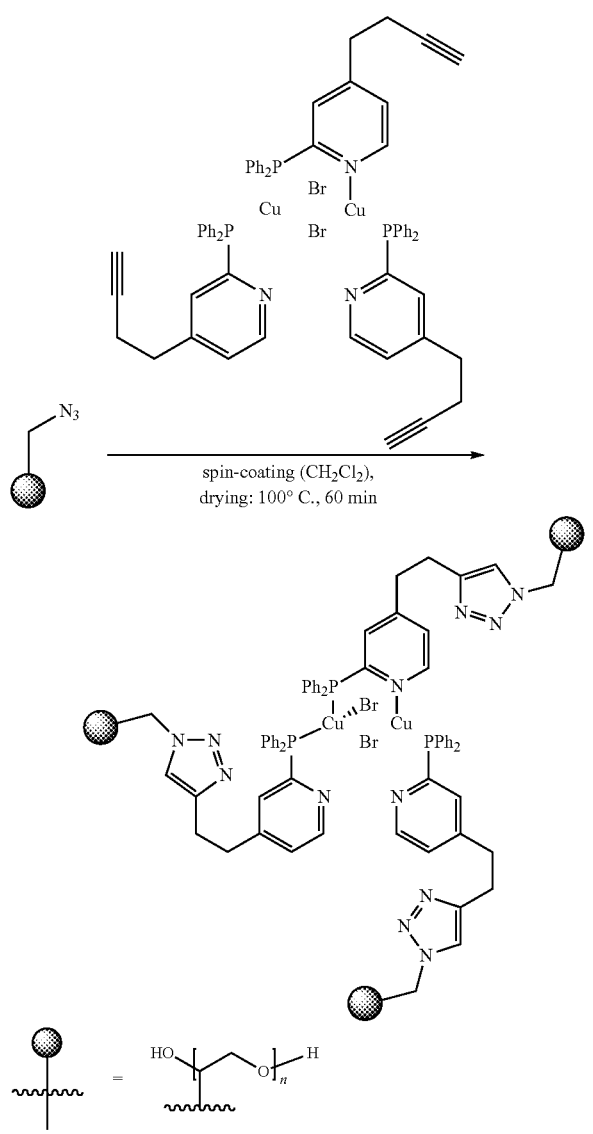

Example 2

The invention relates in a preferred embodiment to the production of novel optoelectronic inks as emitter materials for organic light-emitting diodes as optoelectronic component. In one embodiment, the ink is based on electroluminescent copper(I) complexes, in which diphenylphosphinepyridines, diphenylphosphinechinolines and related heterocycles are used as ligands. These bidentate ligands form polynuclear complexes with copper(I) iodide with a ligand to metal iodide ratio of 3:2.

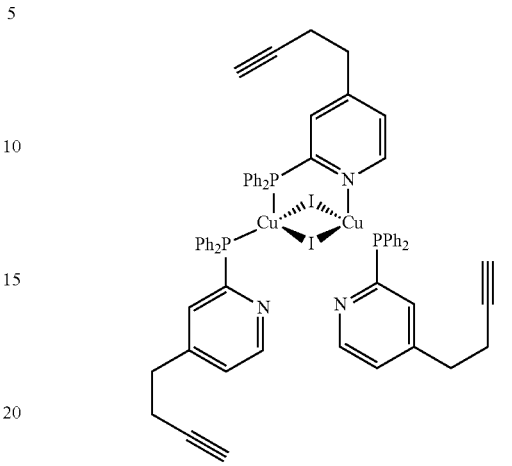

Structure of tris-(4-butinyl-2-diphenyl phosphinopyridine)-bis-(copper iodide)

As shown in experiments, these ligand systems can be substituted with alkyne chains such as 4-butyne and coupled as a copper complex (first reactant with first anchor group) in a click reaction with azides. With this reaction, low-molecular as well as polymeric azides can be converted as a second reactant so that, for example, cross-linked, copper-containing polymers can be synthesized, which combine the electroluminescent properties of the metal complexes with the advantages of the simple liquid processing of the polymers and result in robust, insoluble layers after one baking step.

Furthermore, this reaction can be carried out with other ligand classes. At the same time, further material functions can be implemented into the ink in addition to the cross-linking. Therefore, click-reactions can be used in order to link functional semiconductors (as third reactant), which have hole-transporting or electron-transporting properties, to the complexes. If the anchor group, e.g. the alkyne linker, is linked in conjugation to the organic ligands and aromatic azides are used, the emission color of the complexes, which is based on charge-transfer transitions between the metal ions and the ligands, can be influenced. Since the dimeric complexes each contain three ligands and thus three positions for connection, the complexes can in this way be bound to the polymers as well as bound to hole and electron conductors. The optical, mechanical and electrical properties of the substances obtained that way can for this reason be influenced via the respective composition of the azide mixture. These parameters of the ink can be optimized by robot-supported high-throughput screening methods. With the use of different metal complexes substituted with alkynes, organic light emitting diodes in different colors can be realized, and white-light OLEDS can be achieved by suitable mixture of colors of the corresponding metal complexes.

Accordingly, emitters can be linked with an ideal mixture of hole conductors, electron conductors, and a polymer to an optoelectronic ink.

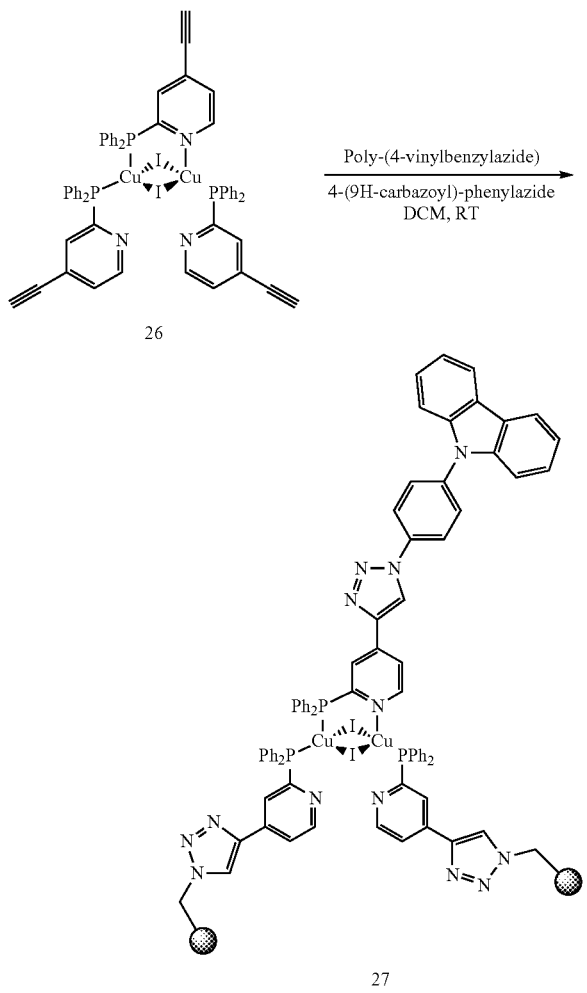

The ball shown in 27 stands for polystyrene, but can also represent any other polymer, oligomer or monomer as second reactant.

In the process, the PyrPHOS complex (pyridyldiphenylphosphine=PyrPHOS) itself serves as a catalyst for the click reaction. By using polymeric azides with a polystyrene or polyethylene glycol backbone a cross-linking occurs by complexation. This can be uses by processing: If a freshly produced mixture of the alkyne complex and the azide polymer is applied to a glass substrate by spincoating or knife-coating and the substrate tempered for one hour at 100° C., cross-linked, insoluble layers are formed.

On these layers additional charge transport layers can be easily applied in further processing steps. As could be shown by photoluminescence spectroscopy, the yellow emission color of the copper-PyrPHOS complexes is influenced neither by variation of the alkyl chains nor by the connection to the polymers. The emission maximum of the PyrPHOS-systems lies at 550 nm. By mixing the composite material with the hole conductor CBP in a single layer assembly, it was shown that the emission color observed by photoluminescence can also be reproduced in an OLED.

Example 3

Knife Coating Application

With the knife coating method, thin layers can be produced by means of a wedge-shaped coating knife. For this purpose, the substance is applied in solution onto the substrate and evenly distributed by means of a slide, which can be controlled with a definite gap width and drawing speed. The films thus produced are dried by heating and a nitrogen flow, so that extremely smooth, defined layers can be produced.

For the production of the thin layers, the polymer dissolved in xylene was mixed in a vial with the metal complex solved in dichloromethane and shortly after mixing was applied as a light cloudy solution to a substrate coated with indium tin oxide (ITO) and PEDOT:PSS. An equimolar stoichiometry was chosen.

The reaction, coating and drying were carried out at various temperatures. Since the whole process was finished after a very short period of time, the samples were subsequently tempered on a heating plate at 100° C. for one hour in order to reach a high yield of the Huisgen reaction. The samples were examined under a UV-lamp as well as by atomic force microscopy. Furthermore, the films were rinsed by immersion in xylene before and after drying for monitoring the reaction. While the cross-linked product is insoluble, the reactants dissolve in this solvent, so that by the resistance of the layers a conclusion about a successful cross-linking can be drawn.

With increasing process temperature the resistance to rinsing increased. After the tempering step, all tested layers were resistant to xylene. The different samples were measured by AFM (atomic force microscopy) in order to examine the morphology of the layers on a nano-scale level.

The impression gained by optical comparison that the properties of the cross-linked samples could not be changed by rinsing was confirmed by atomic force microscopy. In addition, the roughness $R_q$ (standard deviation of the height distribution curve) was determined (according to E. P. Degarmo, J. T. Black, R. A. Kohser, Materials and Processes in Manufacturing, 2003, 9. edition, Wiley, 223). For this, the whole scan area or a section of it in case of impurities were selected. The results are listed in table 2 below.

The roughness is very low for the measured samples with values between −0.53 and 1.64 nm, indicating an excellent morphology of the measured samples.

TABLE 2

Roughness of the AFM-samples. Pinholes appeared in the first four samples, the determination was therefore not carried out over the whole measuring range but over a hole-free area in order to obtain representative results.

| sample | | roughness $R_q$ | in relation to an area of |
|---|---|---|---|
| 80 | 11° C. | 0.66 nm | 0.478 µm² |
| 80 | 11° C. rinsed | 0.99 nm | 0.397 µm² |
| 81 | 25° C. | 0.53 nm | 0.485 µm² |
| 81 | 25° C. rinsed | 0.70 nm | 0.495 µm² |
| 82 | 40° C. | 1.64 nm | 1.000 µm² |
| 82 | 40° C. rinsed | 0.91 nm | 1.000 µm² |

Histograms are shown in FIG. 4 for comparison. Thus, quite sharp, almost Gaussian height distributions resulted. The standard deviation of these distribution curves is specified as $R_q$ in the table.

Example 4

Simultaneous Linking of the Metal Complex as Well as Further Alkynes

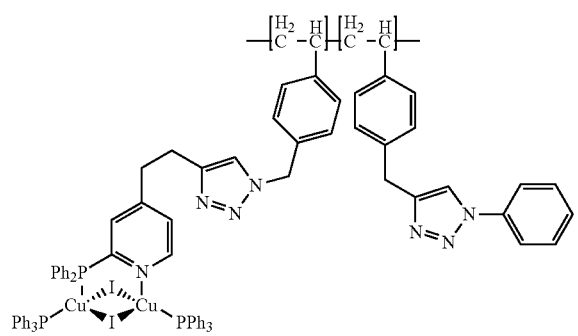

In order to bring copper complexes (first reactant) as emitter as well as charge transport units (third reactant) into a polymer (second reactant) in a simple modular manner, the metal complex, an excess of azide and phenylacetylene were reacted. Both alkynes were linked to the polymer. Furthermore, the product luminesced as expected, thus the complex remained intact.

Example 5

Cu(I)-Catalysis with the PyrPHOS Complexes

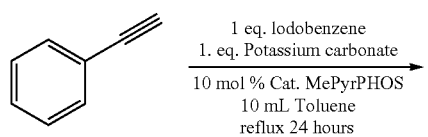

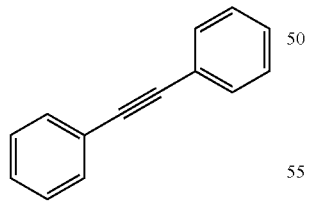

On the one hand, the catalytic potential of the PyrPHOS systems was to be evaluated beyond the Cu(I)-Huisgen reaction. The insoluble, cross-linked PyrPHOS polymers could thus represent a solid-phase catalyst with immobilized Cu(I).

On the other hand, the properties of the metal complexes can be modified with such reactions, e.g.:

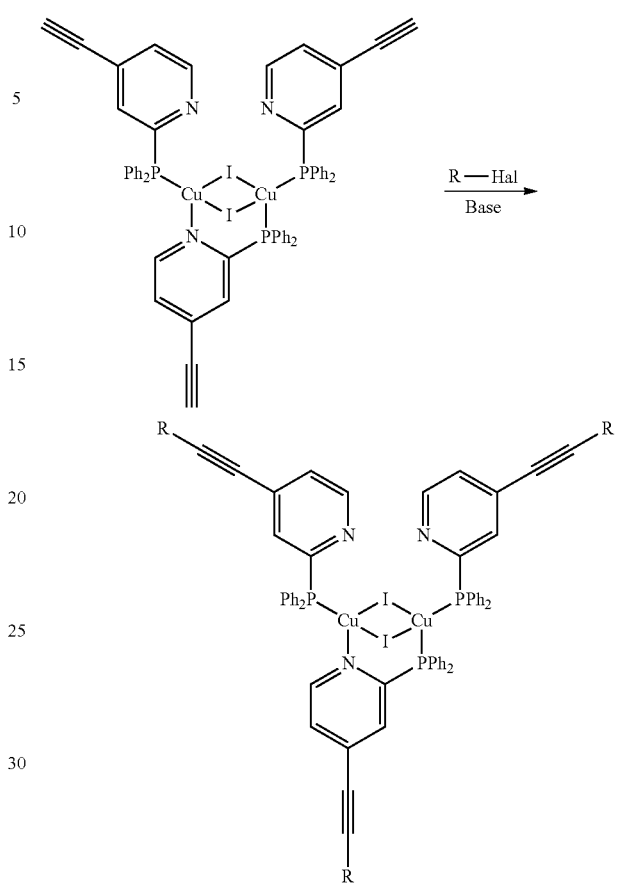

The reaction shown above proceeded with complete conversion (determined with IGC-MS). Furthermore, the catalyst that is insoluble in toluene could be filtered off together with the potassium carbonate and remained intact (preservation of the yellow photoluminescence).

Example 6

Thiol-Ene Reaction

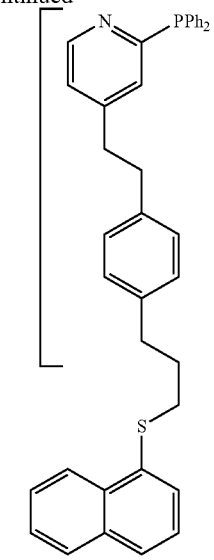

The product shown on the right side luminesced like the reactant shown on the left. The typical odor of a free thiol was lacking after the reaction.

Example 7

Reaction of Heteroleptic Complexes with Charge Transporting Groups

Dinuclear N^α-CuI complexes, which reacted with N-(4-Azidpphenyl)-carbazole:

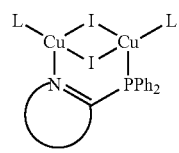

Co-Ligand L:

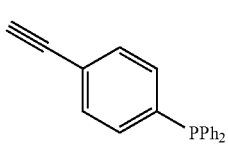

N^P Ligands:

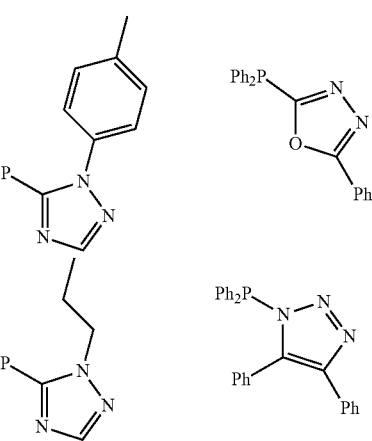

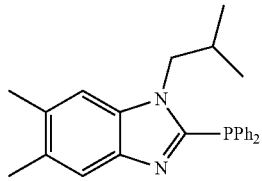 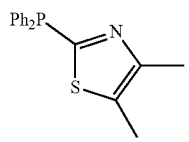

Example 8

Ligands for the Synthesis of Copper Complexes which Enable an Attachment by Huisgen Click Reaction Example 8.1

Synthetic Route to Alkyne-Modified Bisdiphenylphosphino Benzene Derivatives

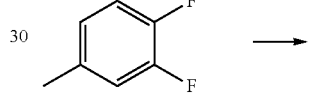

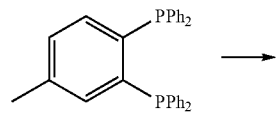

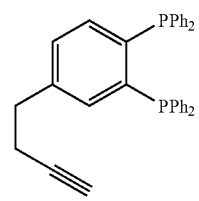

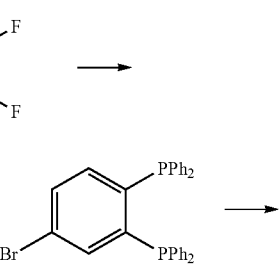

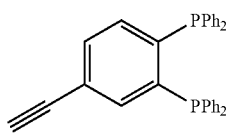

Example 8.2

Different Alkyne-Substituted Ligands which are Suitable for the Preparation of Alkyne-Substituted Copper Complexes

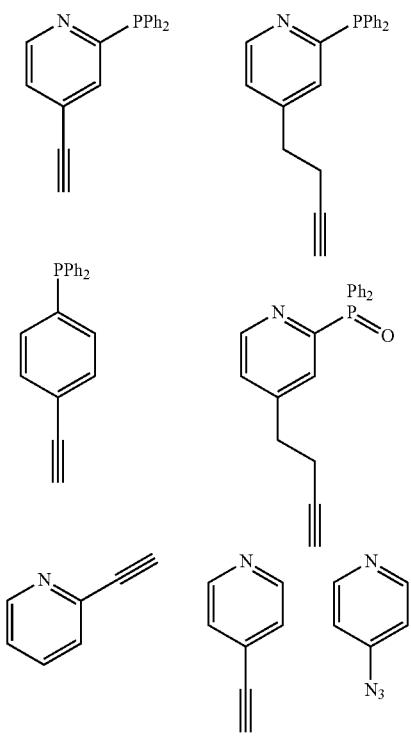

Example 9

Modification of Known Complexes for Achieving Cross-Linkage

By means of the described invention, already known emitter complexes can be modified in order to realize a possibility for cross-linking them. For this purpose, two or more suitable anchor groups are introduced into a complex. For this, all pairs of anchor groups shown in FIG. 2 are suitable.

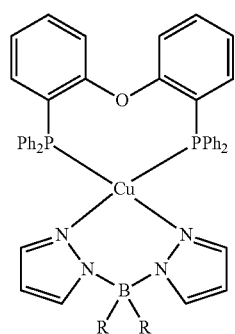

Non-modified structure without anchor groups.

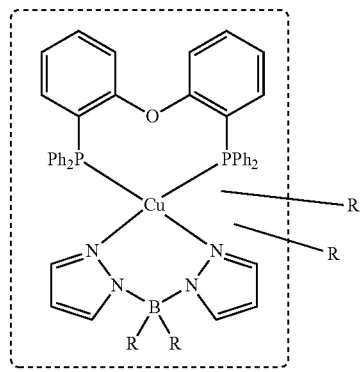

Modified structure with at least two anchor groups.

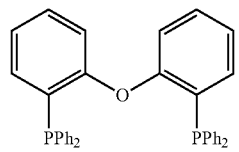

Ligand A

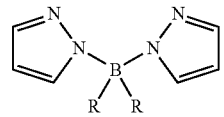

Ligand B

Anchor group R

The basic structure in this figure is already known (Inorg. Chem. 2011, 50, 8293). By substitution with two or more anchor groups, a new structure is formed, which is cross-linkable. All anchor groups R can be attached to one of the ligands A or B or the anchor groups can also be distributed to both ligands, as long as the quorum of two anchor groups per complex unit is achieved.

Example 9.1 Modification of Known Structures

Already known complexes can be modified by including an anchor group in a way that cross-linking is possible. Heteroleptic and homoleptic complexes can be used.

Modifiable, already known structures are listed in the figure. The ligands, which are suitable for a modification according to the invention, are highlighted in boxes. Some ligands such as halides and pseudo-halides are not suitable for such a modification due to chemical reasons. In charged complexes, such as the example from E. J. Org. Chem. in the figure, the luminescent ion, in this case the cation, should be linked.

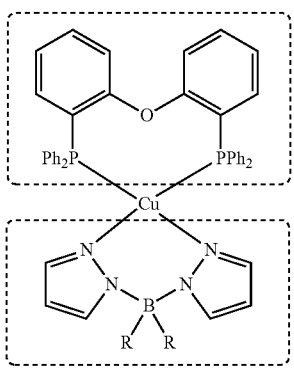
Inorg. Chem. 2011, 50, 8293.
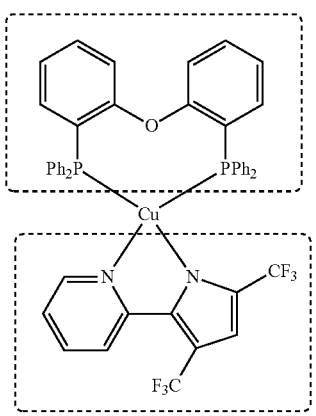
J. Am. Chem. Soc. 2011, 133, 12085.
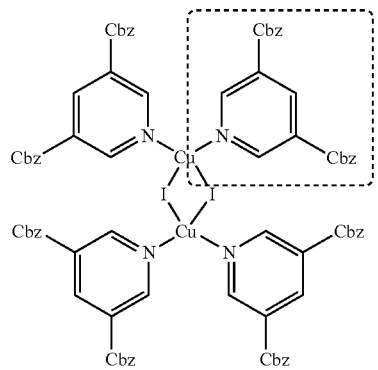
J. Am. Chem. Soc. 2011, 133, 3700.
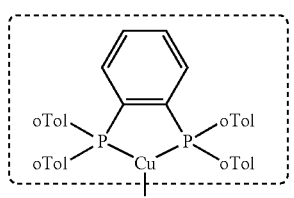
JACS 2011, 133, 10348.
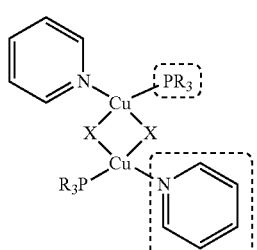
Aust. J. Chem. 1989, 42, 913.
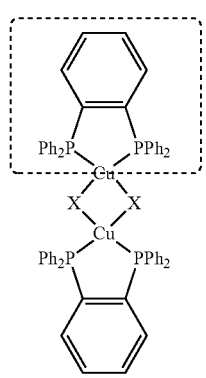
Inorg. Chem. 2007, 46, 1992.
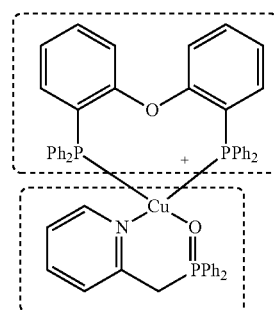
$BF_4^-$ or $PF_6^-$
E. J. Org. Chem., 2010, 4009.
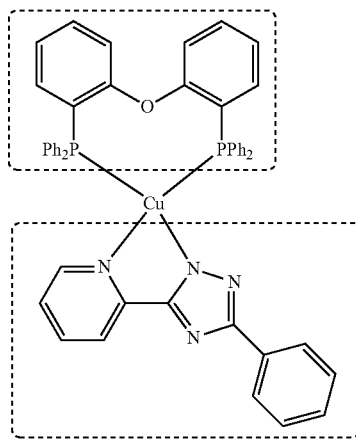
US20100252820

Example 9.2

Synthesis and Spectroscopic Properties of Some Cross-Linkable Cu Complexes

In the following figures, three examples are shown that are suitable for linking to a polymer.

Synthesis of the complexes 9.2 A and 9.2 B: Copper tetrakisacetonitrile tetrafluoroborate (1 mmol, 1 eq.) was provided with the corresponding neocuproine derivatives (1 mmol, 1 eq.) and the phosphines (1 mmol, 1 eq. for 9.2 A and 2 mmol, 2 eq for 9.2 B) in a small glass with stirring bar and septum under nitrogen and solved in 10 mL dry dichloromethane. The reaction mixture was stirred over night, the volume reduced to the half in vacuum and the target compound precipitated by adding dropwise to n-hexane. The identity of the compound was proven by 1H-NMR, 31-P-NMR, elemental analysis and mass spectroscopy.

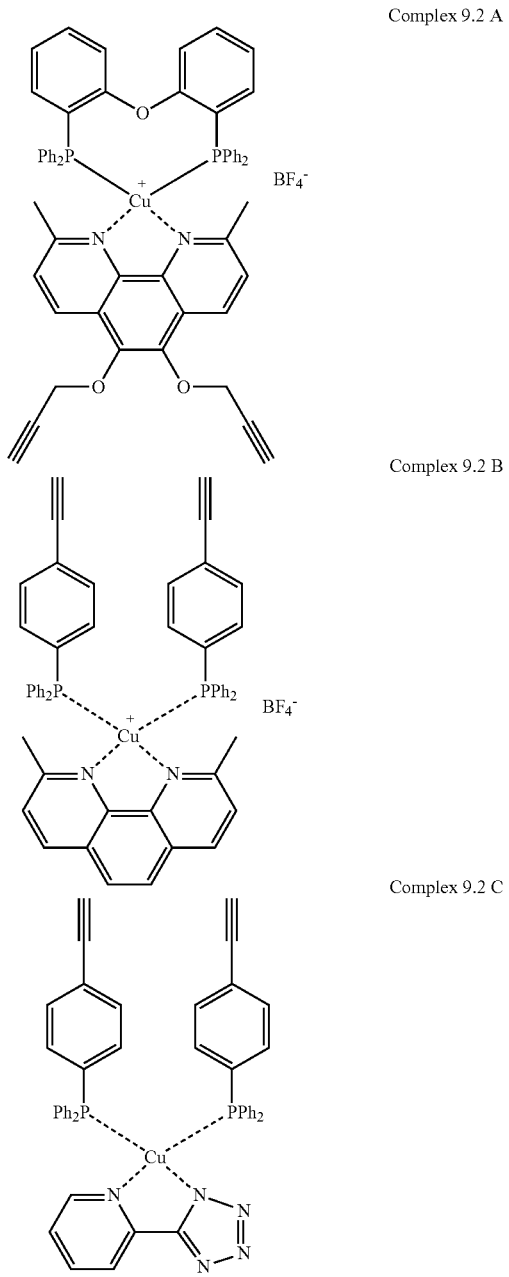

Complex 9.2 A

Complex 9.2 B

Complex 9.2 C

Figure 5:
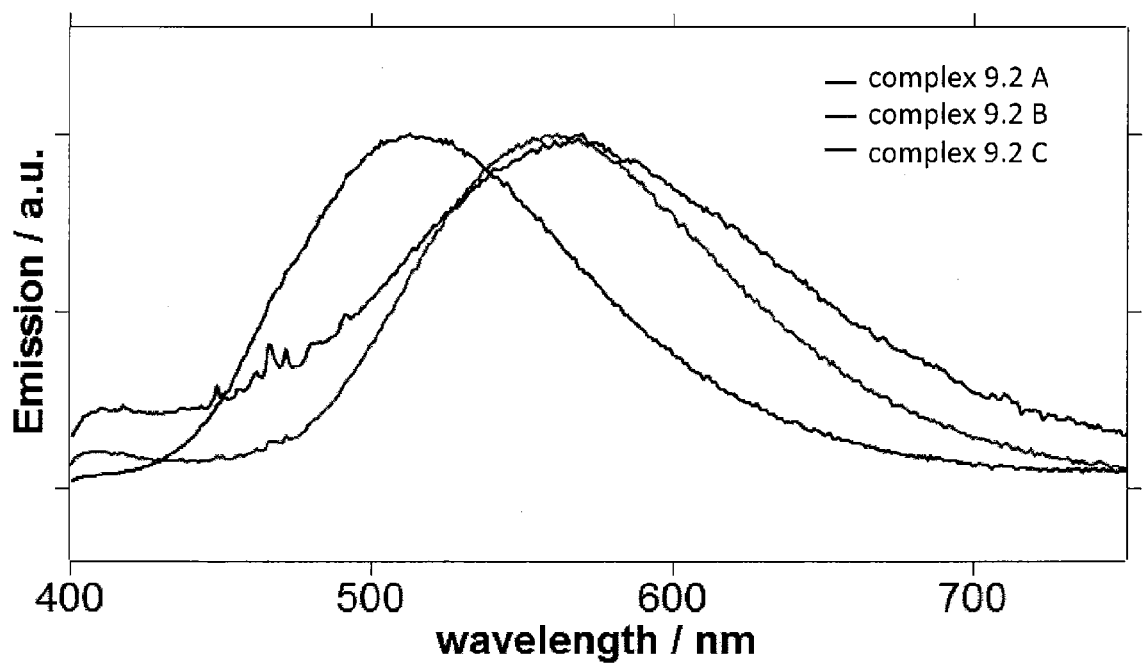
FIG. 5 shows the photoluminescence spectra of the compounds 9.2 A, 9.2 B and 9.2 C powder measurement, room temperature, under normal atmosphere) in accordance with an embodiment of the present invention.

Photoluminescence spectra of the compounds were recorded (powder measurement, room temperature, under normal atmosphere) and are shown in FIG. 5.

Example 10

Application of the Concept to Non-Copper Metal Complexes

The invention also relates to non-copper metal complexes. Thereby, the anchor groups must be adjusted to the chemical properties of the metal complexes to be linked. For some selected metals, such possibilities are shown in the following examples.

Example 10.1

Gold Complexes

Example for a gold emitter:

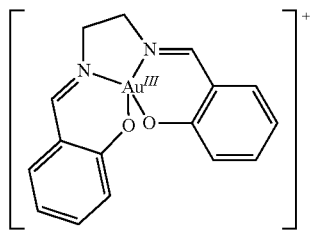

Unmodified, luminescent gold complex.
Orange colored luminescence (570 nm), see *Coord. Chem. Rev.* 2006, 250, 2093-2126

Example for a gold catalysis:

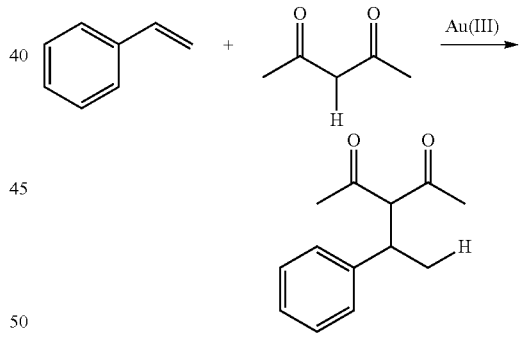

Catalytic example reaction, e.g. *Angew. Chem.*, 2005, 117, 7150
Anchor groups derived therefrom:

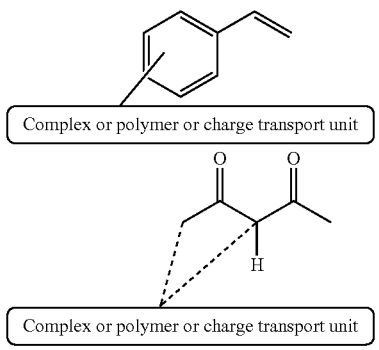

-continued

Modified complex derived therefrom:

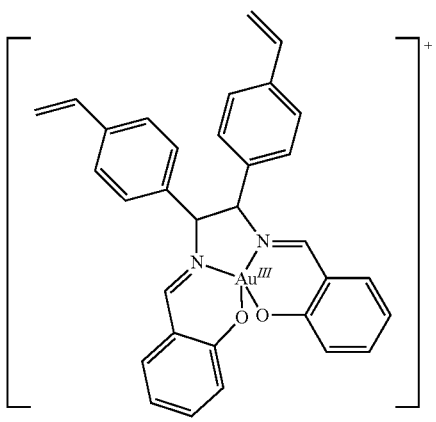

Example 10.2

Ruthenium Complexes

Ruthenium complexes also catalyze cycloadditions between alkynes and azides, but result in 1,5-triazoles in contrary to copper-catalyzed click reactions which result in 1,4-triazoles.

Example for a ruthenium emitter:

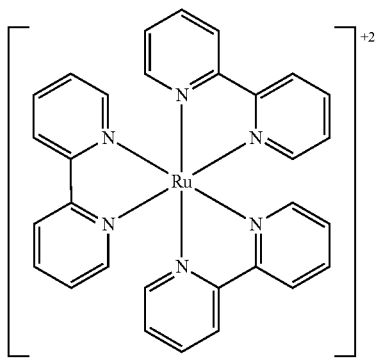

Unmodified, luminescent ruthenium complex.
Red luminescence (614 nm), see *Coord. Chem. Rev.* 2006, 250, 2093-2126

Example for a ruthenium catalysis:

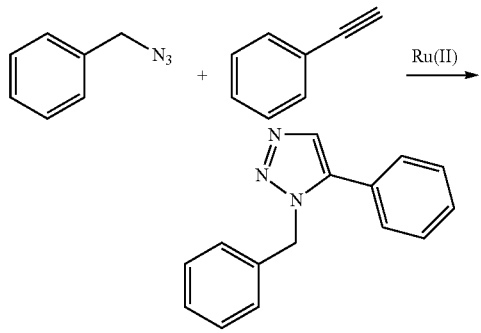

Catalytic example reaction, e.g. *J.Am. Soc.*, 2008, 130, 28, 8923-8930.

-continued

Anchor groups derived therefrom:

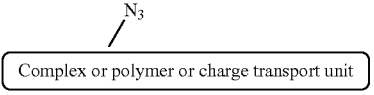

Modified complex derived therefrom:

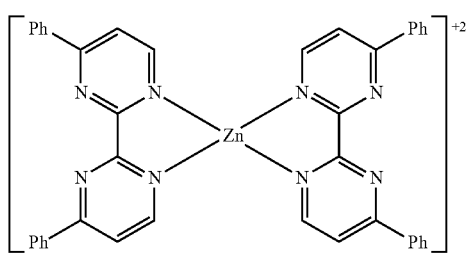

Example 10.3

Zinc Complexes

Example for a zinc emitter:

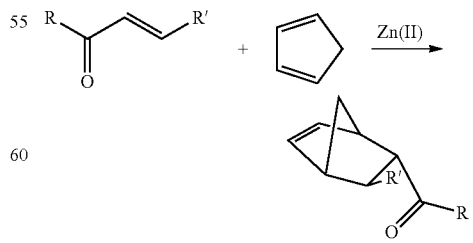

Unmodified, luminescent zinc complex.
Blue luminescence (415 nm), see *Coord. Chem. Rev.* 2006, 250, 2093-2126

Example for a zinc catalysis:

Catalytic example reaction, e.g. *Coord. Chem. Rev.*, 2000, 200-202, 717-772.

Anchor groups derived therefrom:

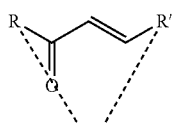

Modified complex derived thereform:

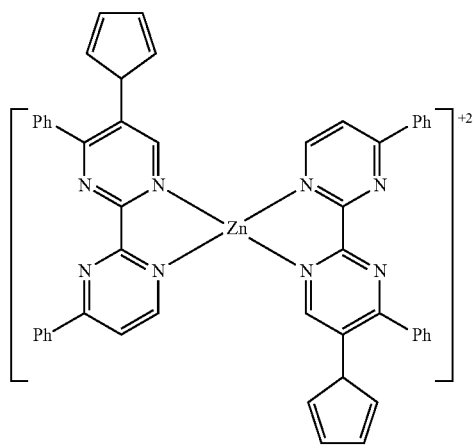

Example 10.4

Platinum Complexes

Example for a platinum emitter:

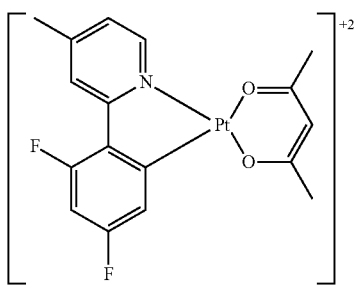

Unmodified, luminescent platinum complex.
see *J. Am. Soc.* 2004, 126, 47, 15388-15389

Example for a platinum catalysis:

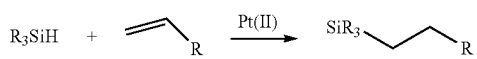

Catalytic example reaction, e.g. *J. Am. Soc.* 196, 108, 23,
7228-7231. (silanes)
L. Pavasi, R. Turan, "Silicon Nanocrystals: Fundamentals,
Synthesis and Applications",
*J. Viley*, 2010, page 165 ff. (silicon nanoparticle)

Anchor groups derived therefrom:

Modified complex derived thereform:

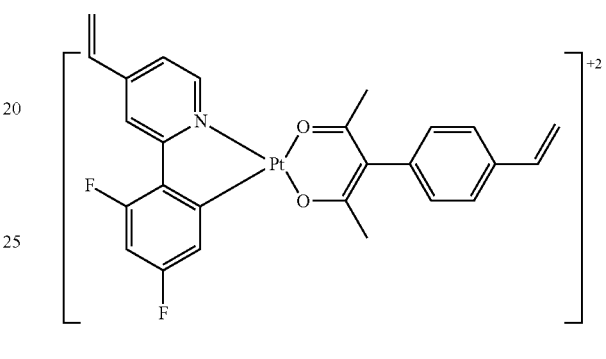

Example 11

Cross-linking of the Cu(I) complex to a polymer via a spacer molecule.

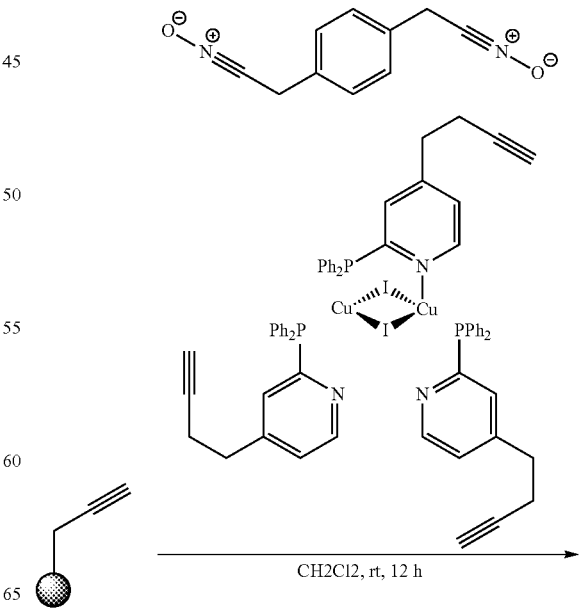

-continued

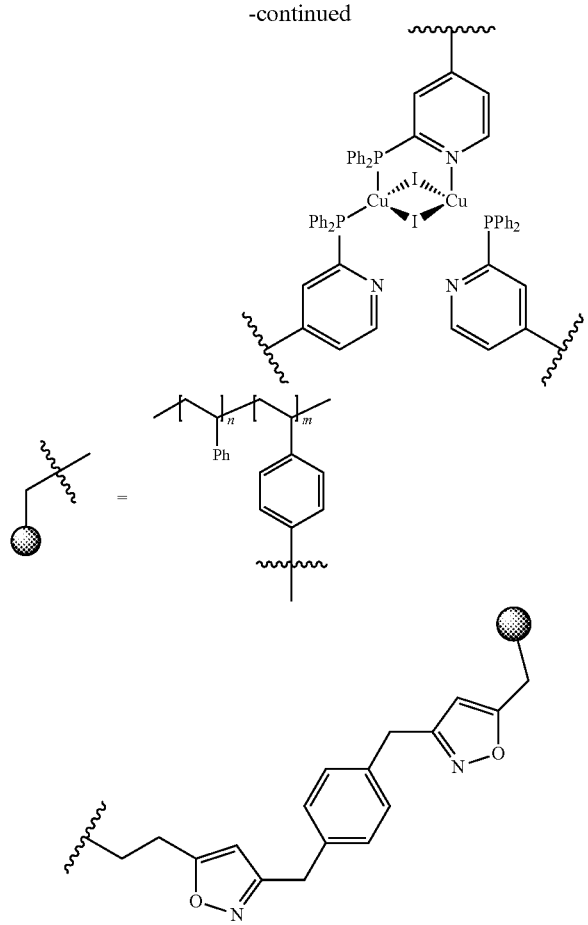

Although illustrative embodiments of the present invention have been described herein with reference to the accompanying drawings, it is to be understood that the invention is not limited to those precise embodiments and that various other changes and modifications ma be made b one skilled in the art without departing from the scope or spirit of the invention.

The invention claimed is:

1. A method for cross-linking of an organic transition metal complex into a multi-dimensional network, comprising:
performing a first reaction which comprises:
a first reactant in the form of the organic transition metal complex; and
a second reactant for formation of the multi-dimensional network;
wherein the organic transition metal complex is cross-linked during the first reaction by formation of covalent bonds to form the multi-dimensional network;
wherein the organic transition metal complex comprises at least two anchor groups of a first anchor group species for the covalent bonding of the organic transition metal complex into the multi-dimensional network and the second reactant comprises at least one anchor group of a second anchor group species;
wherein the cross-linking of the organic transition metal complex proceeds by reaction of each of the at least two anchor groups of the organic transition metal complex with an anchor group of the second reactant;
wherein the cross-linking is not a copolymerization, the copolymerization comprising a reaction in which a plurality of different monomers are cross-linked with each other;
wherein the second reactant and the first reactant are different from each other; and
wherein the second reactant is selected from the group consisting of an oligomer and a polymer wherein the first and the second anchor group species are selected from corresponding pairs of:

anchor A

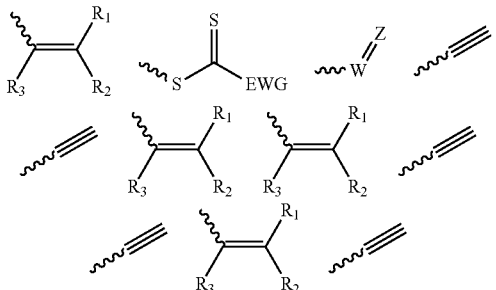

correspond. anchor B

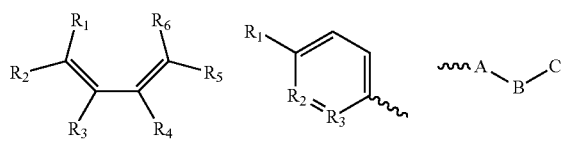

Linkage at any position, any (also different) groups R

Dipolarophile WZ, 1,3-dipole ABC

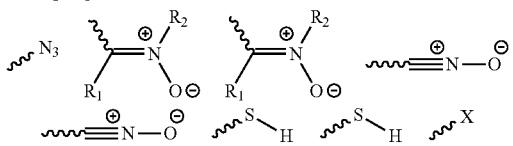

$R_1$-$R_6$ can each independently be hydrogen, a halogen or substituents, which are bound via —OR*, —NR*$_2$ or —SiR*$_3$ as well as alkyl, aryl, heteroaryl, alkenyl, alkynyl groups or substituted alkyl, aryl, heteroaryl and alkenyl groups;
R*=organic group selected from the group consisting of hydrogen, a halogen or deuterium, as well as alkyl, aryl, heteroaryl, alkenyl, alkynyl groups or substituted alkyl, aryl, heteroaryl and alkenyl groups;
Wherein EWG is an electron withdrawing group.

2. The method according to claim 1, wherein the multi-dimensional network is insoluble in a common organic solvent.

3. The method according to claim 1, wherein the first reaction further comprises at least one of a third reactant and a fourth reactant.

4. The method according to claim 3, wherein the third reactant comprises two anchor groups of the second anchor group species, and wherein each of the anchor groups of the third reactant can form a covalent bond with one of the first anchor group.

5. The method according to claim 3, wherein the fourth reactant comprises an anchor group of the first or second anchor group species, and wherein the fourth reactant is for transport or blocking of electrical charges.

6. The method according to claim 1, wherein the first reaction takes place in the presence of a catalyst, and wherein the organic transition metal complex comprises the catalyst.

7. The method according to claim 3, further comprising performing a second reaction for the production of a multi-layer arrangement, the second reaction comprising:
- a fifth reactant in form of the organic transition metal complex; and
- a sixth reactant for formation of the multi-dimensional network;
- wherein the organic transition metal complex is cross-linked by the formation of covalent bonds during the second reaction to form the multi-dimensional network.

8. The method according to claim 1, wherein $R_1$-$R_6$ optionally lead to annulated ring systems.

* * * * *